US00PP36206P2

(12) United States Plant Patent
Hansen

(10) Patent No.: US PP36,206 P2
(45) Date of Patent: Oct. 15, 2024

(54) ***SCHIZACHYRIUM* PLANT NAMED 'BRUSH STROKES'**

(50) Latin Name: *Schizachyrium scoparium*
Varietal Denomination: Brush Strokes

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 18/445,590

(22) Filed: Nov. 7, 2023

(51) Int. Cl.
*A01H 5/12* (2018.01)
*A01H 6/46* (2018.01)

(52) U.S. Cl.
USPC ..... Plt./384

(58) Field of Classification Search
USPC ..... Plt./384

CPC ... A01H 5/12; A01H 5/00; A01H 5/02; A01H 6/46

See application file for complete search history.

(56) References Cited

PUBLICATIONS

Greenhouse Canada Walter Gardens announces New Proven Winners Perennials for the 2023-2024 season, retrieved on Mar. 6, 2024 at https://www.greenhousecanada.com/walter-gardens-announces-new-proven-winners-perennials-for-the-2023-2024-season/, Jan. 20, 2022. (Year: 2022).*

* cited by examiner

*Primary Examiner* — June Hwu

(57) ABSTRACT

A new and distinct plant cultivar of little bluestem plant, *Schizachyrium scoparium* 'Brush Strokes' has a dense, upright habit with long arching lower foliage. Early foliage coloration is bluish-green which develops purplish-grey highlights by early autumn. The flowers remain effective with purplish tinting into winter.

2 Drawing Sheets

Botanical classification: *Schizachyrium scoparium.*
Varietal denomination: 'Brush Strokes'.

STATEMENT REGARDING PRIOR DISCLOSURES UNDER 37 CFR 1.77(b)(6)

No plants of *Schizachyrium* 'Brush Strokes' have been sold or offered for sale anywhere in the world more than one year prior to the filing of this application. The first information about the new plant was displayed on Dec. 1, 2022, as a brief description and photograph, on the website managed by Walters Gardens, Inc. Walters Gardens, Inc. obtained the new plant and all information about the new plant from the inventor.

BACKGROUND OF THE INVENTION

The present invention relates to a new and distinct cultivar of *Schizachyrium scoparium* and will be referred to hereafter by its cultivar name, 'Brush Strokes', the "new cultivar" and "the new plant." 'Brush Strokes' represents a new cultivar of little bluestem, an ornamental grass grown for landscape use.

The new plant was a selection of a single seedling from a cross made in the summer of 2018 between 'Blue Paradise' U.S. Plant Pat. No. 28,145 as the female or seed parent and the proprietary unreleased and unnamed hybrid known only by the breeder code 11-7-x. The seedling was selected among several thousand other seedlings collected from other crosses and others of which were open pollinations of numerous cultivars and selections. Prior to planting in the open field, the seedlings were greenhouse-grown in plugs in the same nursery in Zeeland, MI in 2019. Preliminary evaluation was in the autumn of 2019 using the breeder code 18-4-12, and final evaluation and selection of the new plant was performed in the autumn of 2020.

*Schizachyrium* 'Brush Strokes' has been successfully propagated by culm division at the same nursery in Zeeland, Michigan since the fall of 2020 and since 2021 by sterile plant tissue culture shoot division. The resulting asexually propagated plants have remained stable and true to type for all traits of the original plant in successive generations.

BRIEF SUMMARY OF THE INVENTION AND COMPARISON

The following traits have been repeatedly observed and represent the characteristics of the new cultivar which in combination distinguish *Schizachyrium scoparium* 'Brush Strokes' from all other little bluestem plants known to the inventor:

1. Early and summer foliage coloration of blue-green;
2. Early autumn foliage develops purplish-grey highlights;
3. Dense culms with upright habit with arching lower foliage.

*Schizachyrium* 'Brush Strokes' compares most closely with the Little Bluestem cultivars: 'Blue Paradise' U.S. Plant Pat. No. 28,145, 'Carousel' U.S. Plant Pat. 20,948, 'Smoke Signal' U.S. Plant Pat. No. 27,433, 'Twilight Zone' U.S. Plant Pat. No. 27,432 and 'MinnblueA' U.S. Plant Pat. No. 17,310.

'Blue Paradise' has a slightly shorter habit and develops a deep wine color to the foliage in autumn. 'Carousel' has a shorter habit and the foliage develops an orangish-brown coloration. 'Smoke Signal' has a narrower slower growing habit and the foliage becomes scarlet reddish in autumn. 'Twilight Zone' has a shorter habit, the foliage begins turning purplish earlier, and it also flowers later than either of the nearest comparison cultivars. 'MinnblueA' is much taller and spreading in habit, and more purple with less blue-green in the foliage earlier in the season.

The male parent was taller with deeper purple foliage coloration in autumn.

The comparison below in Table 1 shows a more succinct differentiation between other known little bluestem cultivars.

TABLE 1

| CULTIVAR | HEIGHT | WIDTH | SUMMER FOLIAGE COLOR | AUTUMN FOLIAGE COLOR | HABIT |
|---|---|---|---|---|---|
| 'Blue Paradise' | 100 cm | 70 cm | silver-blue | deep wine-red | upright |
| 'Brush Strokes' | 116 cm | 105 cm | powder blue | purplish-grey | upright |
| 'Carousel' | 75 cm | 75 cm | orange-brown | mahogany, reddish-orange | compact rounded |
| 'MinnblueA' | 130 cm | 75 cm | light blue with highlights of red and purple | burgundy-tipped blue | tall upright |
| 'Smoke Signal' | 110 cm | 45 cm | scarlet-red | deep reddish-purple | upright |
| 'Twilight Zone' | 112 cm | 75 cm | silvery mauve-purple | bright purple | upright arching |

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, intensity, source, and direction may cause the appearance of minor variations in color. The plant in the photographs is a three-year-old plant grown in a full-sun trial garden in Zeeland, Michigan, USA with supplemental water and minimal fertilizer when needed.

DETAILED BOTANICAL DESCRIPTION

Figure 1:
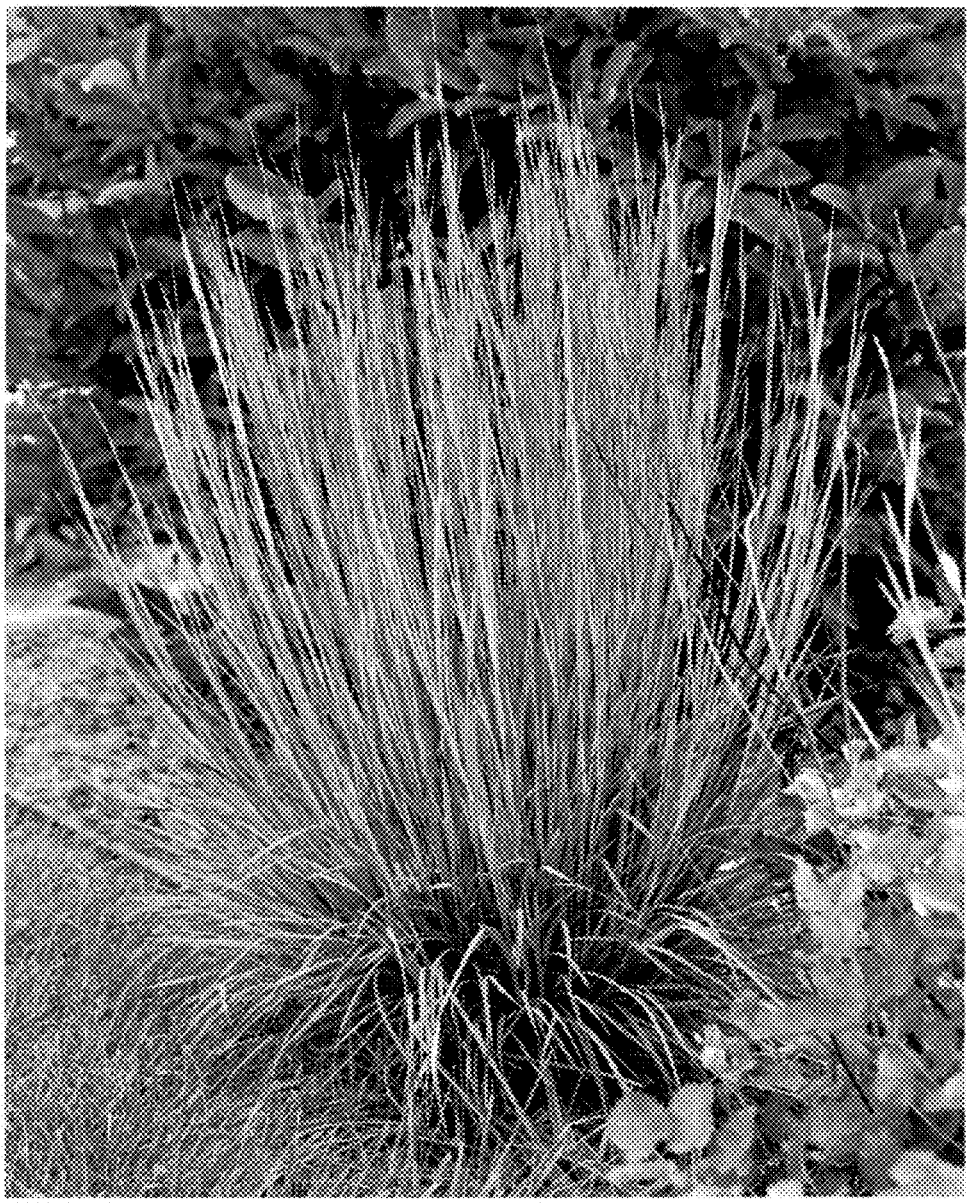
FIG. 1 shows the plant habit and foliage in mid-summer.
Figure 2:
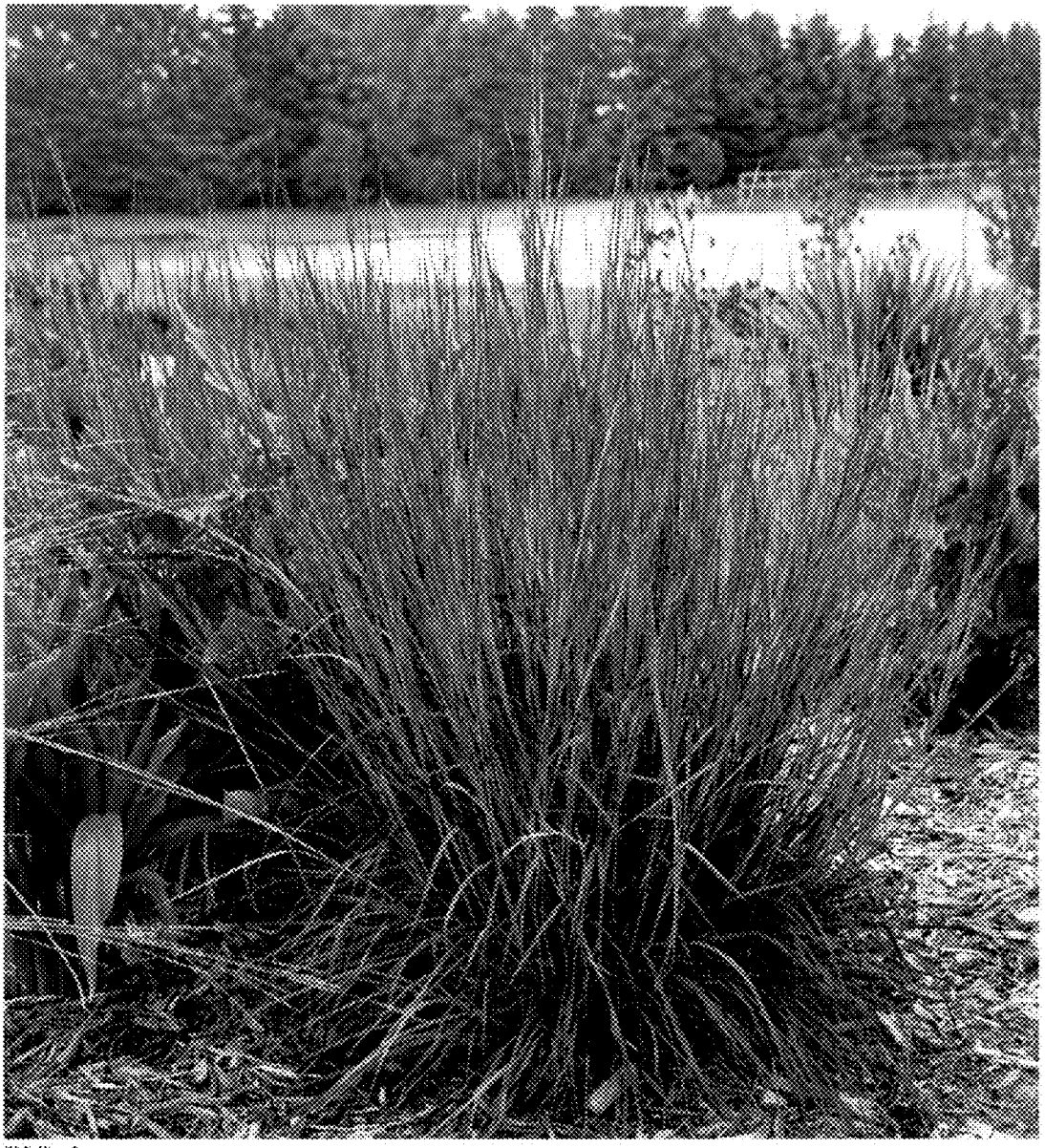
FIG. 2 shows the plant with foliage in early autumn.

The following detailed description of *Schizachyrium scoparium* 'Brush Strokes' is of a three-year-old plant grown in a full-sun trial field with supplemental water and fertilizer in Zeeland, Michigan. The color references are in accordance with the 2001 edition of The Royal Horticultural Society Colour Chart except where common color terms of ordinary dictionary reference are used. The phenotype may vary slightly with different environmental conditions, such as temperature, light, fertility, moisture, and maturity levels, but without any change in the genotype.

*Parentage*.—the female or seed parent is 'Blue Paradise'; the male or pollen parent is 11-7-x.

*Growth rate*.—very rapid, finishing in a 65 mm container from a stage 3 tissue culture plant in two months; producing roots in tissue culture in about three weeks.

*Rooting habit*.—normal, branching; fibrous, wiry, deeply rooted up to about 90 cm long; color of roots near white to tan depending on soil type.

*Plant habit*.—herbaceous perennial grass, compact with upright culms and dense arching foliage.

*Plant size*.—about 116 cm tall and about 105 cm wide.

*Culm*.—about 140 per plant; round in cross-section; thin, wiry, strong; glaucous, glabrous; with foliage to near distal end; internode pithy.

*Culm size*.—to about 116 cm long, average about 97 cm long and 3 mm at base; about 4 cm to 10 cm of culm exposed between leaves.

*Culm color*.—seasonally and position variable; summer—lower portion covered with sheath nearest RHS 145C, middle portion variable, nearest RHS 178C and nearest RHS 183C, upper portion nearest RHS183A; autumn—lower portion nearest RHS 176B, middle and upper portion nearest RHS 183D.

*Nodes*.—about five to six per culm; swollen to about 4 mm diameter of lower nodes; glabrous, glaucous; internode length between about 20 cm on middle internodes and about 7 cm in distal internodes, average about 11 cm.

*Node color*.—between RHS N187A and RHS 187A by mid-summer and into winter.

*Foliage*.—leaves flat, alternate, linear, entire, glabrous, glaucous; apex narrowly acute, base sheathing and usually open with long split extending to near node; sheath portion up to 15 cm long on lower leaves and 7 cm on upper leaves; largest leaves about 49 cm long and about 5 mm wide; upper leaves about 15 cm long and about 2.5 mm across; five to six per culm.

*Foliage color*.—varies with season; on adaxial early summer between RHS 138A and RHS 138B, and abaxial nearest RHS 138C; late-summer and autumn adaxial nearest RHS N187A, abaxial between RHS N187A and RHS N187B; winter color adaxial and abaxial between RHS 199D and RHS 177D.

*Venation*.—parallel.

*Vein color*.—same as surrounding tissue of both abaxial and adaxial.

*Ligule*.—membranous, fimbriate, about 1.5 mm long and width equal to leaf.

*Ligule color*.—between RHS 165C and RHS 165D.

*Flower description*.—branched raceme at distal five to seven nodes; flower period late autumn in Western Michigan; remaining effective into winter.

*Rachis*.—glaucous, glabrous; up to about 55 cm long, and about 0.5 mm diameter; average about 40 cm long and 0.5 mm diameter; frequently with two or three rachillae per node.

*Rachis and Rachilla color*.—between RHS 183C and RHS 183D.

*Spikelets*.—in pairs adpressed to rachilla; one sessile and one pedicellate; pedicellate spikelet sterile and reduced; sessile spikelet fertile, about 10 mm long and about 1.5 mm across.

*Glumes*.—paired; lemma surrounding inner palea; acute apex with bristle; adhering to caryopsis; color nearest RHS 187A.

*Bristle*.—single; stiff; to about 12 mm long; straight; color nearest RHS 187A.

*Lemma*.—about 7 mm long and about 1 mm wide; acute apex, color nearest RHS 187A.

*Palea*.—about 6 mm long and about 1 mm wide; acute apex; color nearest RHS 161D.

*Reproductive*.—Androecium; usually three. Anther: oblong; basifixed; about 4 mm long and about 0.5 mm diameter; color nearest RHS 187A. Filament: very fine, about 0.2 mm diameter and about 2 mm long; color nearest RHS 155D. Pollen; abundant; color nearest 187B. Gynoecium: one. Style: plumose, about 2.5 mm long and about 1 mm diameter; color nearest RHS 187A. Stigmas: numerous, nonsecund, surrounding style; color nearest RHS 187A.

*Seed*.—caryopsis; enclosed in glume; ovoid with broadly acute apex; less than 1 mm long and 0.7 mm diameter; color varies with maturity between RHS 200C and RHS N199D.

*Pest and disease resistance*.—generally free of pests and diseases, susceptibility or resistance beyond that typical of little bluestem has not been observed.

*Hardiness*.—hard from U.S.D.A. zones 3 to 9; able to withstand adverse weather and still remain upright; like most little bluestem the new plant is able to withstand some drought once established.

It is claimed:

1. A new and distinct ornamental cultivar of little bluestem plant, *Schizachyrium scoparium* plant named 'Brush Strokes', as herein described and illustrated, for landscaping the garden en masse or individually.

* * * * *